United States Patent
Pan et al.

(10) Patent No.: US 7,848,790 B2
(45) Date of Patent: Dec. 7, 2010

(54) SYSTEM AND METHOD OF IMAGING USING A VARIABLE SPEED FOR THORAX IMAGING

(75) Inventors: Tin-Su Pan, Brookfield, WI (US); Steve Woloschek, Franklin, WI (US); H. David He, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1105 days.

(21) Appl. No.: 10/260,006

(22) Filed: Feb. 28, 2002

(65) Prior Publication Data

US 2003/0163039 A1   Aug. 28, 2003

(51) Int. Cl.
*A61B 5/05* (2006.01)

(52) U.S. Cl. .......................... 600/425; 600/428; 378/8; 378/15; 378/19

(58) Field of Classification Search ................. 382/131; 378/901, 209, 4, 20–21, 8, 15, 5, 94; 600/425, 600/428, 415, 420, 407; 250/491.1
See application file for complete search history.

(56) References Cited

U.S. PATENT DOCUMENTS

| | | | | |
|---|---|---|---|---|
| 4,034,224 A | * | 7/1977 | Heavens et al. | 378/20 |
| 5,046,003 A | * | 9/1991 | Crawford | 378/15 |
| 5,262,946 A | * | 11/1993 | Heuscher | 378/15 |
| 5,383,231 A | * | 1/1995 | Yamagishi | 378/15 |
| 5,386,446 A | | 1/1995 | Fujimoto et al. | |
| 5,928,148 A | * | 7/1999 | Wang et al. | 600/420 |
| 6,023,494 A | * | 2/2000 | Senzig et al. | 378/4 |
| 6,061,420 A | * | 5/2000 | Strong et al. | 378/4 |
| 6,185,271 B1 | * | 2/2001 | Kinsinger | 378/19 |
| 6,233,478 B1 | * | 5/2001 | Liu | 600/428 |
| 6,266,553 B1 | * | 7/2001 | Fluhrer et al. | 600/428 |
| 6,442,228 B1 | * | 8/2002 | Woloschek et al. | 378/8 |
| 6,466,640 B1 | * | 10/2002 | Taguchi | 378/15 |
| 6,504,893 B1 | * | 1/2003 | Flohr et al. | 378/8 |

(Continued)

FOREIGN PATENT DOCUMENTS

DE    199 57 082 A1    8/2001

(Continued)

OTHER PUBLICATIONS

Spiral Volumetric CT with Single-Breath-Hold Technique, Continuous Transport, and Continuous Scanner Rotation, Kalendar et al, Radiology 176:181-183(1990).*

(Continued)

*Primary Examiner*—Brian Casler
*Assistant Examiner*—Baisakhi Roy
(74) *Attorney, Agent, or Firm*—Ziolkowski Patent Solutions Group, SC

(57) ABSTRACT

A system and method of medical imaging using a variable speed patient positioning table are provided. The patient positioning table is configured to operate at a plurality of table speeds during acquisition of data from a selected region, such as the thorax region baying predefined cardiac and non-cardiac regions. In a non-cardiac region, the table is controlled to move at one speed and when the cardiac region is detected, the table is controlled to move at another speed, preferably faster than in the cardiac region to speed data acquisition and eliminate motion artifacts.

24 Claims, 2 Drawing Sheets

U.S. PATENT DOCUMENTS 6,535,821 B2 * 3/2003 Wang et al. .................. 702/19

FOREIGN PATENT DOCUMENTS

| EP | 1 072 224 A2 | 1/2001 |
|---|---|---|
| JP | 220135 A | 8/1993 |
| JP | 314162 A | 12/1998 |

OTHER PUBLICATIONS

Hui hu: "Multi-slice helical CT: Scan and reconstruction", Milwaukee WI; Med.Phys. 26 (1) Jan. 1999.

Parker, Dennis I: Optimization of short scan convolution reconstruction in fan beam CT; CH1751-7/82/0000/0199$00.75 © 1982 IEEE.

* cited by examiner

SYSTEM AND METHOD OF IMAGING USING A VARIABLE SPEED FOR THORAX IMAGING

BACKGROUND OF THE INVENTION

The present invention relates generally to medical imaging and, more particularly, to a system and method of imaging a thorax using a variable speed patient-positioning table, preferably in computed tomography systems.

Typically, in computed tomography (CT) imaging systems, an x-ray source emits a fan-shaped beam toward an object, such as a patient. The beam, after being attenuated by the patient, impinges upon an array of radiation detectors. The intensity of the attenuated beam radiation received at the detector array is typically dependent upon the attenuation of the x-ray beam by the patient. Each detector element of the detector array produces a separate electrical signal indicative of the attenuated beam received by each detector element. The electrical signals are transmitted to a data processing unit for analysis which ultimately results in the formation of an image.

Generally, the x-ray source and the detector array are rotated with a gantry within an imaging plane and around the patient. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator.

In one known CT imaging system used to image a thorax, imaging is conducted by moving a patient table through a gantry at a constant speed. Generally, the constant table speed is determined by matching the speed of the table to the phase of a patient's cardiac cycle with EKG gating. Problems arise, however, using such a system since the table speed is required to move at a very slow speed throughout imaging in order to have sufficient coverage of the heart at a prescribed phase. Using a slow table speed throughout imaging has several disadvantages such as patient discomfort, limited patient accessibility to the CT system, and a higher x-ray radiation dose to the patient for slower acquisition for the same coverage area. One proposed solution to this problem considered increasing the table speed during imaging. This solution, however, is not suitable for thorax imaging because of the occurrence of motion artifacts. Motion artifacts are caused by motion of the imaged thorax or a part of the imaged thorax, such as the heart, during the imaging sequence causing a blurring in the reconstructed image in the regions where motion occurs. It is well known in the art that motion artifacts can be minimized during imaging of the thorax if the imaging sequence is gated to the cardiac cycle of the patient.

It would therefore be desirable to have a CT imaging system capable of speeding up the imaging time to image a thorax region of a patient without generating motion artifacts in the reconstructed image.

BRIEF DESCRIPTION OF THE INVENTION

The present invention provides a variable speed table for a CT imaging system and method of use that solves the aforementioned drawbacks.

A system and method of computer tomography imaging using a variable speed patient positioning table are provided. The system includes a high frequency electromagnetic energy projection source to project towards an object, such as a patient. A detector receives the high frequency energy attenuated by the patient. A plurality of electrical interconnects is configured to transmit detector output to a data processing system to produce a visible display. A rotatable gantry has a patient positioning table passing therethrough. The patient positioning table is configured to operate at a plurality of table speeds during acquisition of a set of data from a selected region, such as the thorax region of a patient. A cardiac imaging method of acquiring a set of data values during imaging of the cardiac scanning region and at least one non-cardiac scanning region to reconstruct an image is also provided.

In accordance with one aspect of the present invention, a cardiac imaging method includes the steps of positioning a patient on a variable speed table of an imaging device, determining a cardiac scanning region and at least one non-cardiac scanning region, moving the variable speed table at a primary velocity during imaging of the cardiac scanning region, and moving the variable speed table at a secondary velocity during imaging of the at least one non-cardiac scanning region. The method further includes the steps of acquiring data during imaging of the cardiac scanning region and the at least one non-cardiac scanning region, and reconstructing an image based on the data acquired at differing table speeds.

In accordance with another aspect of the invention, a computed tomography system is provided. This system includes a projection source to project towards an object and a detector to receive high frequency electromagnetic energy attenuated by the object. The detector produces outputs that are transmitted to a data processing system by a plurality of electrical interconnects. The system further includes a computer capable of producing a visual display based upon the photodiode outputs transmitted to the data processing system and control a speed of the patient positioning table in response to detection of a particular region of the object. This system also includes a patient positioning table having variable speed capability and configured to operate at a plurality of table speeds during acquisition of a set of data from a selected region.

In accordance with yet another aspect of the invention, a computer-readable medium having stored thereon a computer program which, when executed by a computer, will cause the computer to determine a cardiac scanning region and a non-cardiac scanning region, move a variable speed table at a primary velocity in the cardiac scanning region, and move the variable speed table at a secondary velocity in the non-cardiac scanning region. The computer program also has instructions to acquire a set of imaging data in the cardiac scanning region and in the non-cardiac scanning regions and reconstruct an image based on data acquired using at least two different table speeds.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

A system and method is described for a computed tomography (CT) system capable of imaging a thorax. It will be appreciated by those of ordinary skill in the art that the present invention is equally applicable for use with single-slice or other multi-slice configurations. Moreover, the present invention will be described with respect to the detection and conversion of x-rays. However, one of ordinary skill in the art will further appreciate, that the present invention is equally applicable in other imaging modalities.

Figure 1:
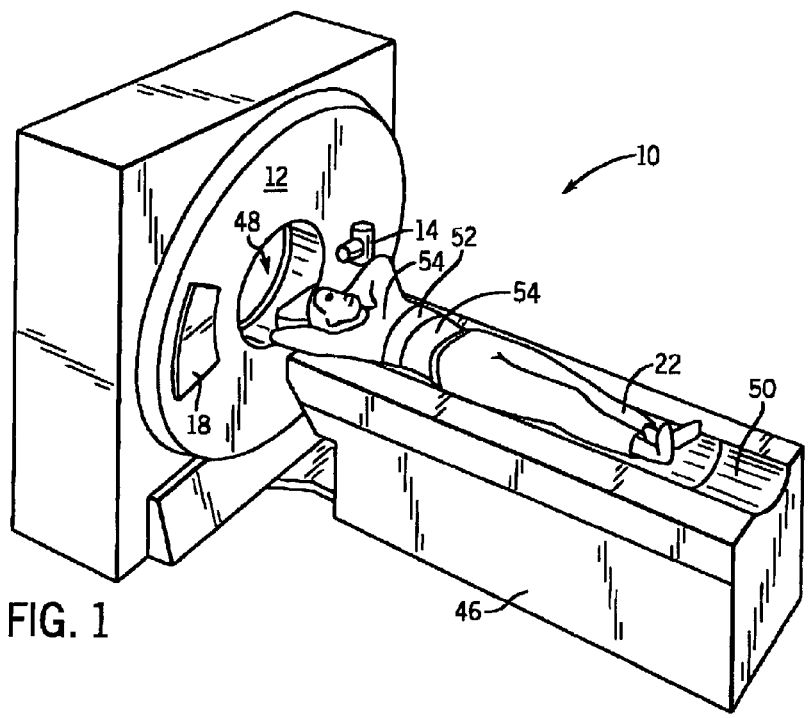
FIG. 1 is a perspective view of a CT imaging system.
Figure 2:
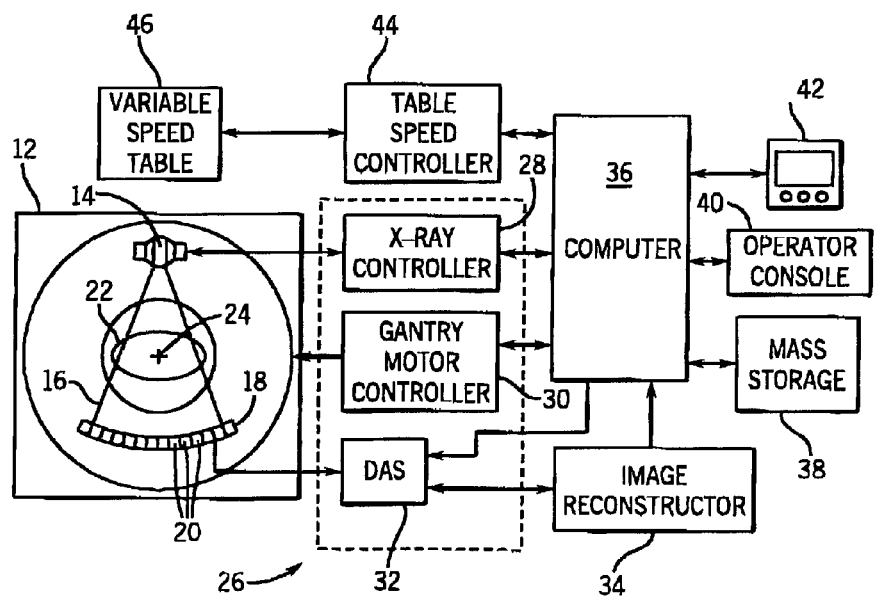
FIG. 2 is a perspective block schematic diagram of the system illustrated in FIG. 1.

Referring to FIGS. 1 and 2, an exemplary computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24. Detector array 18 and detectors 20 can be any number of high frequency electromagnetic energy detectors, such as gas-filled, scintillation cell-photodiode, and semiconductor detectors as is know to those skilled in the art of detector design.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high-speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table speed controller 44 which controls a variable speed table 46 during imaging of a patient 22 within gantry 12. Particularly, table 46 is configured to move a patient 22 through a gantry opening 48 along an axis 50.

In operation, a patient 22 or object is positioned within the CT scanner or imaging device 10 on the variable speed table 46 with a selected region of the patient chosen for scanning adjacent to the gantry 12. A technician or health-care operator enters input into the operator console 40, thereby defining a scanning region, such as the thorax which includes cardiac region 52 and non-cardiac regions 54. The computer 36 then instructs the table speed controller 44 to move the variable speed table 46 at a first table speed towards the gantry opening 48 causing the patient 22 to enter therein. As one of the non-cardiac regions 54 of the patient 22 enters the gantry opening 48, control mechanism 26 causes x-ray controller 28 to provide power and timing signals to x-ray source 14 while the gantry motor controller 30 causes rotation of gantry 12 to begin the imaging scan of the non-cardiac region 54.

Table speed controller 44 continues to move the patient 22 through the gantry opening 48 to conduct an imaging scan of the cardiac region 52 at a second table speed, different than the first. The table is then adjusted again when other non-cardiac region 54 of the thorax is reached. The first table speed is preferably configured to move faster than the second table speed since motion artifacts are not created by contraction of the heart muscle in the non-cardiac regions 54. Consequently, scanning times for imaging of the thorax are reduced. After scanning the thorax, detectors 20 send the x-ray data acquired from the cardiac region 52 and non-cardiac regions 54 to DAS 32 and image reconstructor 34 for digitalization and image reconstruction. Computer 36 then processes the digitized x-ray data to provide a reconstructed image of the cardiac region 52 and non-cardiac regions 54 on display 42.

Figure 3:
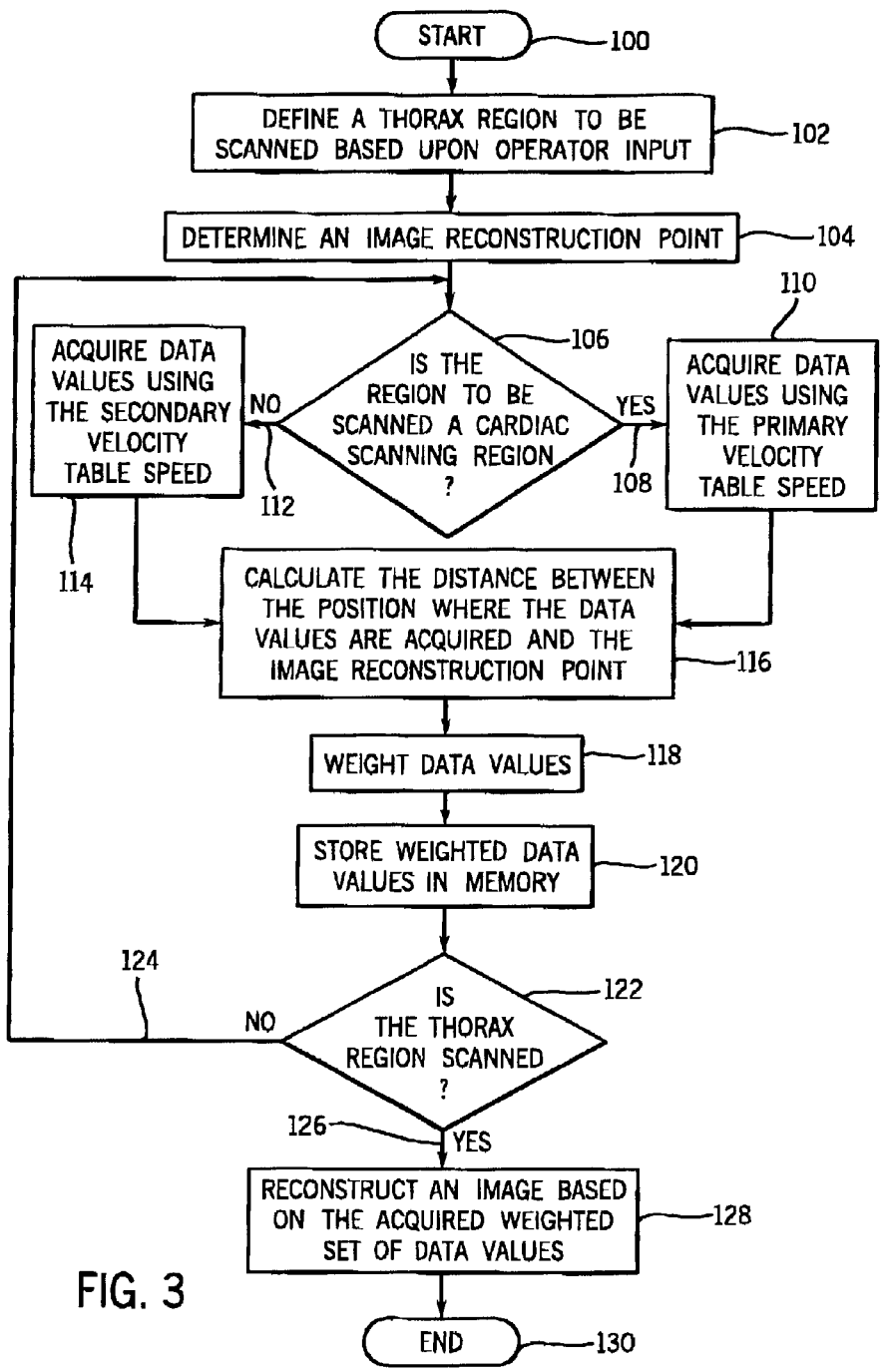
FIG. 3 is a flow chart showing a process of the present invention and implemented in the system of FIG. 1.

Referring to FIG. 3, a flowchart illustrating the steps of a method and acts associated with a computer program in accordance with the present invention are shown. The method and/or computer program is initiated at 100 by a technician or CT scanner operator who provides input into the computer to define a set of regions to be scanned 102, such as a cardiac scanning region and adjacent non-cardiac scanning regions of a patient's thorax. Generally, such operator entered input can include a starting position and an ending position along a common axis, such as axis 50 of FIG. 1. An image reconstruction point is then calculated 104, which is preferably centrally positioned between the starting and ending input positions, or end points of the defined thorax region. The method decides at 106 whether the region to be scanned is a cardiac scanning region, and if so 108, acquires data values with the patient table moving at a primary velocity 110. For a non-cardiac scanning region 112, data values are acquired with the patient table moving at a secondary velocity 114. As previously discussed, the variable speed table is preferably configured to move at a faster velocity during scanning in non-cardiac scanning regions and a slower velocity in the cardiac scanning region where motion artifacts can occur due to motion of the heart. In a preferred embodiment, the scanning of the cardiac scanning region has a primary velocity that is equivalent to an EKG gating speed of the scanned patient with the EKG gating speed determined according to a diastole phase of the patient's cardiac cycle.

After acquiring data values 110, 114, a distance between the position where each data value is acquired and the image reconstruction location or point is calculated 116. Using the calculated distances, the data values are weighted 118 according to the distance of each of the data values from the image reconstruction location and stored in memory of the computer 120. The method next proceeds to determine whether the entire thorax region has been scanned 122. If the thorax region has not been scanned 124, then the method loops back to step 106 and again determines whether the region to be scanned is a cardiac region 106. The method then continues to collect data values for the identified region of the thorax.

Data values are acquired as the variable speed table moves through the gantry, with the acquired data values for the thorax scanning region taken with the table moving at the generally faster secondary velocity in the non-cardiac regions, and at the slower primary velocity in the cardiac region where the EKG gating speed of a diastole phase of a patient's cardiac cycle determines the primary velocity in the cardiac region. Data values acquired further away from the image reconstruction location are accorded less weight during image reconstruction providing an improved reconstructed image. After the data values are acquired, they can be combined to form a single set of data values, and then summed for image reconstruction.

Upon completion of scanning of the thorax region 126, an image is reconstructed using the combined set of acquired and weighted data values 128. A reconstructed image can then be shown on a cathode ray tube display, or alternatively, stored in memory for later use. The method then ends at 130.

In one alternative embodiment, the transition of the variable speed table can be transitioned at step 124 by incrementally changing the speed, in a linear transgression, or in a step-wise incrementation, or any other transition method that permits scanning to occur in the non-cardiac regions at a faster rate than in the cardiac region. The scanning time required to image a patient is thereby reduced as compared to the time spent scanning a patient at a primary velocity determined by a patient's cardiac cycle.

As previously discussed and in accordance with one aspect of the present invention, a cardiac imaging method comprises the steps of positioning a patient on a variable speed table of an imaging device, determining a cardiac scanning region and at least one non-cardiac scanning region, and moving a variable speed table at a primary velocity during imaging of the cardiac scanning region and at a secondary velocity during imaging of the at least one non-cardiac scanning region. The method further includes the steps of acquiring data during imaging of the cardiac scanning region and the at least one non-cardiac scanning region, and reconstructing an image of the region scanned based on the data acquired at differing table speeds.

In accordance with another aspect of the invention, a computed tomography system is provided capable of imaging human anatomy, such as a thorax. This system includes a high frequency electromagnetic energy projection source to project high frequency energy towards an object or patient and a scintillator array having a plurality of scintillators to receive high frequency electromagnetic energy attenuated by the object/patient. A photodiode array is optically coupled to the scintillator array and is configured to detect light energy emitted therefrom. The photodiode array produces outputs that are transmitted to a data processing system by a plurality of electrical interconnects. The system further includes a computer capable of producing a visual display based upon the photodiode outputs transmitted to the data processing system and control a speed of the patient positioning table in response to detection of a particular region of the object. This system also includes a patient positioning table having variable speed capability and configured to operate at a plurality of table speeds, such as a primary and secondary velocity, during acquisition of data from a selected region.

In accordance with yet another aspect of the invention, a computer-readable medium having stored thereon a computer program which, when executed by a computer, will cause the computer to determine a cardiac scanning region and a non-cardiac scanning region, move a variable speed table at a primary velocity in the cardiac scanning region, and move the variable speed table at a secondary velocity in the non-cardiac scanning region or regions. The computer program also has instructions to acquire data of the cardiac scanning region and the non-cardiac scanning region, and reconstruct an image based on the data acquired at more than one table speed.

The present invention has been described in terms of the preferred embodiment, and it is recognized that equivalents, alternatives, and modifications, aside from those expressly stated, are possible and within the scope of the appending claims.

The invention claimed is:

1. A cardiac imaging method comprising the steps of:
   positioning a patient on a variable speed table of an imaging device;
   determining, along a common axis, a starting position and an ending position of each of a cardiac scanning region and at least one non-cardiac scanning region to be imaged in a single scan;
   moving the variable speed table at a primary velocity during imaging of the cardiac scanning region;
   moving the variable speed table at a secondary velocity, different from the primary velocity, during imaging of the at least one non-cardiac scanning region, wherein the secondary velocity is at a speed greater than the primary velocity;
   acquiring data during imaging of the cardiac scanning region and the at least one non-cardiac scanning region in the single scan; and
   reconstructing an image based on the data acquired in the single scan at differing table speeds.

2. The method of claim 1 further comprising the step of transitioning the variable table speed incrementally during changes in the speed of the variable table speed.

3. The method of claim 1 wherein the primary velocity is an EKG gating speed of the patient.

4. The method of claim 3 wherein the EKG gating speed is determined according to a diastole phase of a patient's cardiac cycle.

5. The method of claim 1 further comprising the step of weighting the acquired data according to a distance between a position where each data value is acquired and an image reconstruction location.

6. The method of claim 5 wherein the weighting of the acquired data is reduced as the distance between the position where each data is acquired and the image reconstruction location increases.

7. The method of claim 1 wherein the imaging device includes a CT scanner.

8. A computed tomography system comprising:
   a high frequency electromagnetic energy projection source to project high frequency energy towards an object;
   a detector to receive high frequency electromagnetic energy attenuated by the object;
   a plurality of electrical interconnects configured to transmit detector outputs to a data processing system;
   a patient positioning table having variable speed capability and configured to operate at a plurality of table speeds during acquisition of data from a selected region, the selected region including a starting position and an ending position of a cardiac scanning region input by a technician and including a non-cardiac scanning region; and
   a computer programmed to:
      calculate an image reconstruction point that is centrally positioned about the starting position and the ending position;
      control the patient positioning table during a single scan to operate at a first table speed in the cardiac scanning region and at a second table speed, different from the first table speed, in the non-cardiac region; and
      produce a visual display based upon the detector outputs transmitted to the data processing system about the image reconstruction point.

9. The system of claim 8 wherein the selected region is a thorax region of a patient.

10. The system of claim 8 wherein the second table speed is greater than the first table speed.

11. The system of claim 8 further comprising a control configured to detect a change between the cardiac scanning region and the non-cardiac scanning region and vary the speed of the patient positioning table in response thereto.

12. The system of claim 11 wherein the control causes the patient positioning table to have one of an incremental change and a linear change in patient positioning table speed during changes in the patient positioning table speed in the selected region.

13. The system of claim 8 wherein the first table speed is an EKG gating speed determined according to a diastole phase of a patient's cardiac cycle.

14. The system of claim 8 wherein the computer defines a location of an image reconstruction according to an operator entered input.

15. The system of claim 14 wherein the operator entered input includes a starting position and an ending position sharing a common axis for the acquisition of data.

16. The system of claim 14 wherein the data is weighted according to the distance of each acquired data value to the location of the image reconstruction.

17. A non-transitory computer-readable medium having stored thereon a computer program which, when executed by a computer, will cause the computer to:

determine a cardiac scanning region from a user-defined region of a subject, and a non-cardiac scanning region from another user-defined region of the subject, both regions to be imaged in a single scan;

move a variable speed table at a primary velocity in the cardiac scanning region during image acquisition that is determined from an EKG gating speed of a diastole phase of the subject, wherein the primary velocity is greater than a secondary table velocity;

move the variable speed table at the secondary velocity in the non-cardiac scanning region during image acquisition;

acquire a set of imaging data in the cardiac scanning region and in the non-cardiac scanning region in a single scan; and reconstruct an image based on data acquired in the single scan.

18. The computer-readable medium of claim 17 wherein the computer program stored thereon causes the computer to determine an image reconstruction location between a pair of operator entered inputs.

19. The computer-readable medium of claim 18 wherein the image reconstruction location is centrally positioned between the pair of operator entered inputs.

20. The computer-readable medium of claim 18 wherein the computer program stored thereon causes the computer to weight the acquired imaging data according to a distance from a position at which each data value is acquired to the image reconstruction location.

21. The computer-readable medium of claim 20 wherein the weighting of each acquired data value decreases as the distance from the position at which each data value is acquired to the image reconstruction location increases.

22. The computer-readable medium of claim 21 wherein the weighted data values are summed to reconstruct an image.

23. The computer-readable medium of claim 17 wherein the primary velocity is an EKG gating speed of a patient determined according to a diastole phase of the patient's cardiac cycle.

24. The computer-readable medium of claim 17 wherein the primary velocity is less than the secondary velocity.

* * * * *

UNITED STATES PATENT AND TRADEMARK OFFICE
CERTIFICATE OF CORRECTION

| | | |
|---|---|---|
| PATENT NO. | : 7,848,790 B2 | Page 1 of 1 |
| APPLICATION NO. | : 10/260006 | |
| DATED | : December 7, 2010 | |
| INVENTOR(S) | : Pan et al. | |

It is certified that error appears in the above-identified patent and that said Letters Patent is hereby corrected as shown below:

Cover Page, (57), Abstract, line 5, delete "baying" and substitute therefore -- having --.

Signed and Sealed this
Eighth Day of February, 2011

David J. Kappos
*Director of the United States Patent and Trademark Office*